United States Patent
Hennen et al.

(10) Patent No.: US 8,322,233 B2
(45) Date of Patent: Dec. 4, 2012

(54) SELF-FLUSHING BOTTLE IN-LINE FLUID SAMPLER

(75) Inventors: James M. Hennen, Plymouth, MN (US); William E. Allen, Alexandria, IN (US)

(73) Assignee: MTS Systems Corporation, Eden Prairie, MN (US)

( * ) Notice: Subject to any disclaimer, the term of this patent is extended or adjusted under 35 U.S.C. 154(b) by 578 days.

(21) Appl. No.: 12/392,458

(22) Filed: Feb. 25, 2009

(65) Prior Publication Data

US 2010/0212439 A1 Aug. 26, 2010

(51) Int. Cl.
*B01L 3/00* (2006.01)
(52) U.S. Cl. ................................. 73/864.91
(58) Field of Classification Search .............. None
See application file for complete search history.

(56) References Cited

U.S. PATENT DOCUMENTS

| | | | |
|---|---|---|---|
| 4,425,810 A * | 1/1984 | Simon et al. .......... | 73/863.11 |
| 4,611,777 A * | 9/1986 | Ireland et al. ......... | 248/371 |
| 5,251,495 A | 10/1993 | Kuhner | |
| 5,370,005 A | 12/1994 | Fjerdingstad | |
| 7,100,461 B2 | 9/2006 | Bradley | |
| 2005/0167547 A1 | 8/2005 | McLellan | |

FOREIGN PATENT DOCUMENTS

| | | |
|---|---|---|
| DE | 4335368 | 4/1995 |
| EP | 1076233 | 2/2001 |
| WO | WO 92/05420 | 4/1992 |

OTHER PUBLICATIONS

Two sheets of drawings. Illustration and procedure for a fluid sampling device used in the U.S. more than one year prior to the filed of the application.
Official Search Report of the European Patent Office in counterpart foreign application No. PCT/US2010/025336 filed Feb. 25, 2010.
Written Opinion of the European Patent Office in counterpart foreign application No. PCT/US2010/025336 filed Feb. 25, 2010.

* cited by examiner

*Primary Examiner* — Peter Macchiarolo
*Assistant Examiner* — Alex Devito
(74) *Attorney, Agent, or Firm* — Steven M. Koehler; Westman, Champlin & Kelly, P.A.

(57) ABSTRACT

A hydraulic fluid sampler and a method for obtaining a hydraulic fluid sample includes a sample container holder configured to support a sample container mounted thereto in an inverted position and a non-inverted position. In the inverted position, the sample container holder is configured to flush the sample container with hydraulic fluid so as to flush away any contaminates that may be present. In the non-inverted position, the sample container holder is configured to fill the sample container with hydraulic fluid.

24 Claims, 9 Drawing Sheets

SELF-FLUSHING BOTTLE IN-LINE FLUID SAMPLER

BACKGROUND

The discussion below is merely provided for general background information and is not intended to be used as an aid in determining the scope of the claimed subject matter.

The performance and operational life of hydraulically operated or powered systems, such as but not limited to hydraulically operated actuator based material and component test systems, are directly dependent upon the quality of hydraulic fluid used in such systems. In general, fluid deterioration and contamination are of particular concern. Fluid deterioration starts as "additive deterioration." Additives present in hydraulic fluid are particularly susceptible to chemical and physical changes arising from mixing fluids, entrapped air and high temperatures. Additive deterioration then leads to breakdown of the hydraulic fluid. On the other hand, contamination of the hydraulic fluid such as when the fluid contains hard metallic particles can severely damage hydraulic pumps and servovalves, particularly when the particle size is larger than the clearance between lubricated surfaces.

Periodic sampling and then testing of the hydraulic fluid used in a system contributes significantly to increased uptime and better performance of hydraulic systems. Sampling includes drawing off of a small portion of the hydraulic fluid present in the system into a small vessel such as a glass bottle. Problems however can arise if the sample itself becomes contaminated, for example, due to the location at which the sample is taken from the system, prior contamination of the sampling equipment and/or sample container, or other mistakes made by the sampling technician. In view that maintenance of the system such as removing and replacing the hydraulic fluid in the system will be determined based on testing of the sample taken, it is important that the hydraulic sample is a true and accurate representation of the system hydraulic fluid and that it be particularly free of any extraneous contamination.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the background.

An aspect of the invention is a hydraulic fluid sampler that includes a sample container holder configured to support a sample container mounted thereto in an inverted position and a non-inverted position. In the inverted position, the sample container holder is configured to flush the sample container with hydraulic fluid so as to flush away any contaminates that may be present. In the non-inverted position, the sample container holder is configured to fill the sample container with hydraulic fluid.

In an advantageous embodiment, the sampler includes a frame to which the sample container holder is moveably mounted so as to allow the sample container to obtain the inverted and non-inverted positions. In one embodiment, a swivel that allows fluid flow therethrough is provided to allow rotation of the sample container holder so that sample container obtains the inverted and non-inverted positions. In a further embodiment, the sample container holder is disposed between two upstanding vertical supports wherein two swivels are provided to allow rotation of the sample container holder.

The sample container can include a first orifice and a second orifice. The first orifice can be configured to flush the sample container with hydraulic fluid when the sample container is in the inverted position, while the second orifice is configured to receive the flushing hydraulic when the sample container is in the inverted position, the second orifice being fluidly connected to the drain line.

In another advantageous embodiment, the hydraulic fluid sampler can include device adapted to secure the frame to a surface. The device can be a magnetic base, suction cup, heavy weight or the like.

Another aspect of the present invention is a method for obtaining a hydraulic fluid sample. The method includes: mounting a sample container to a sample container holder; connecting the sample container holder to the system in order to obtain hydraulic fluid therefrom; positioning the sample container holder such that the sample container is in an inverted position; flushing the sample container with hydraulic fluid while the sample container is in an inverted position; and after flushing, positioning the sample container holder such that the sample container is in a non-inverted position and filling the sample container with a sample of hydraulic fluid.

In one embodiment, the sample container holder is rotatably mounted to a frame and wherein positioning in the method comprises rotating the sample container holder relative to the frame.

In another embodiment, the method further includes releasably securing the frame to a surface.

DETAILED DESCRIPTION

Figure 1:
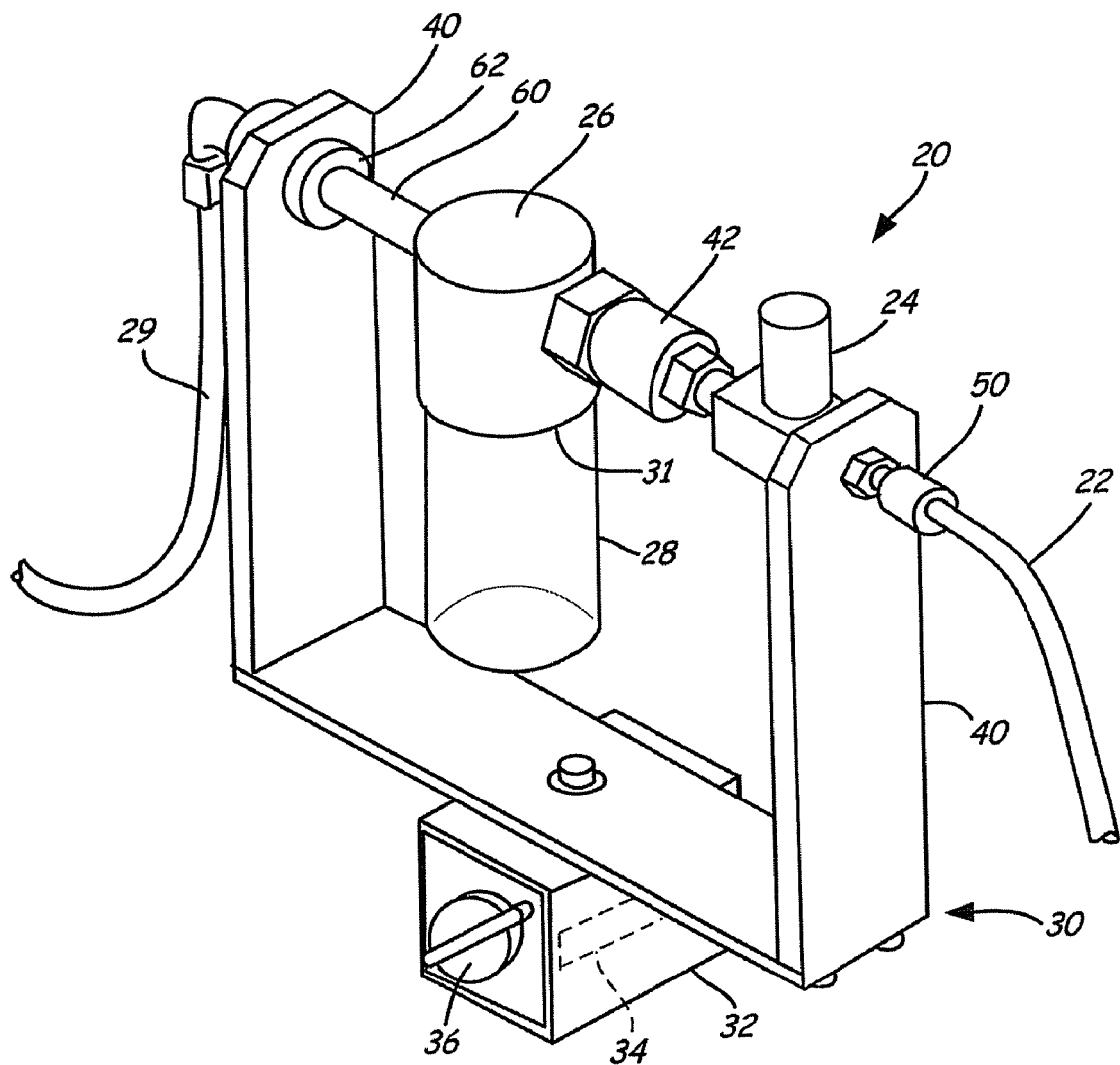
FIG. 1 is a perspective view of a first embodiment of a fluid sampler in a non-inverted position.
Figure 2:
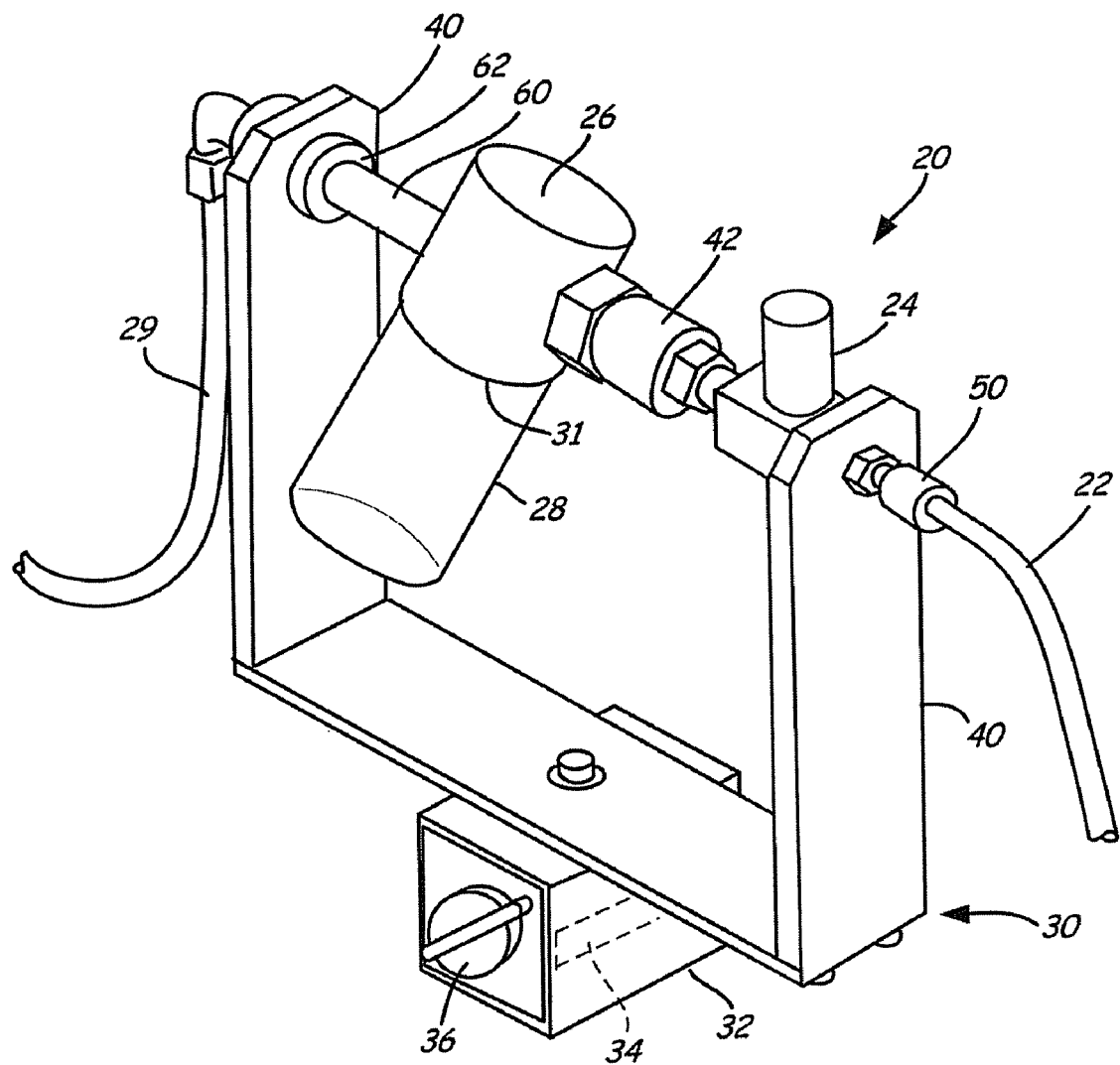
FIG. 2 is a perspective view of the first embodiment of a fluid sampler in a position transitioning between the non-inverted position and an inverted position.
Figure 3:
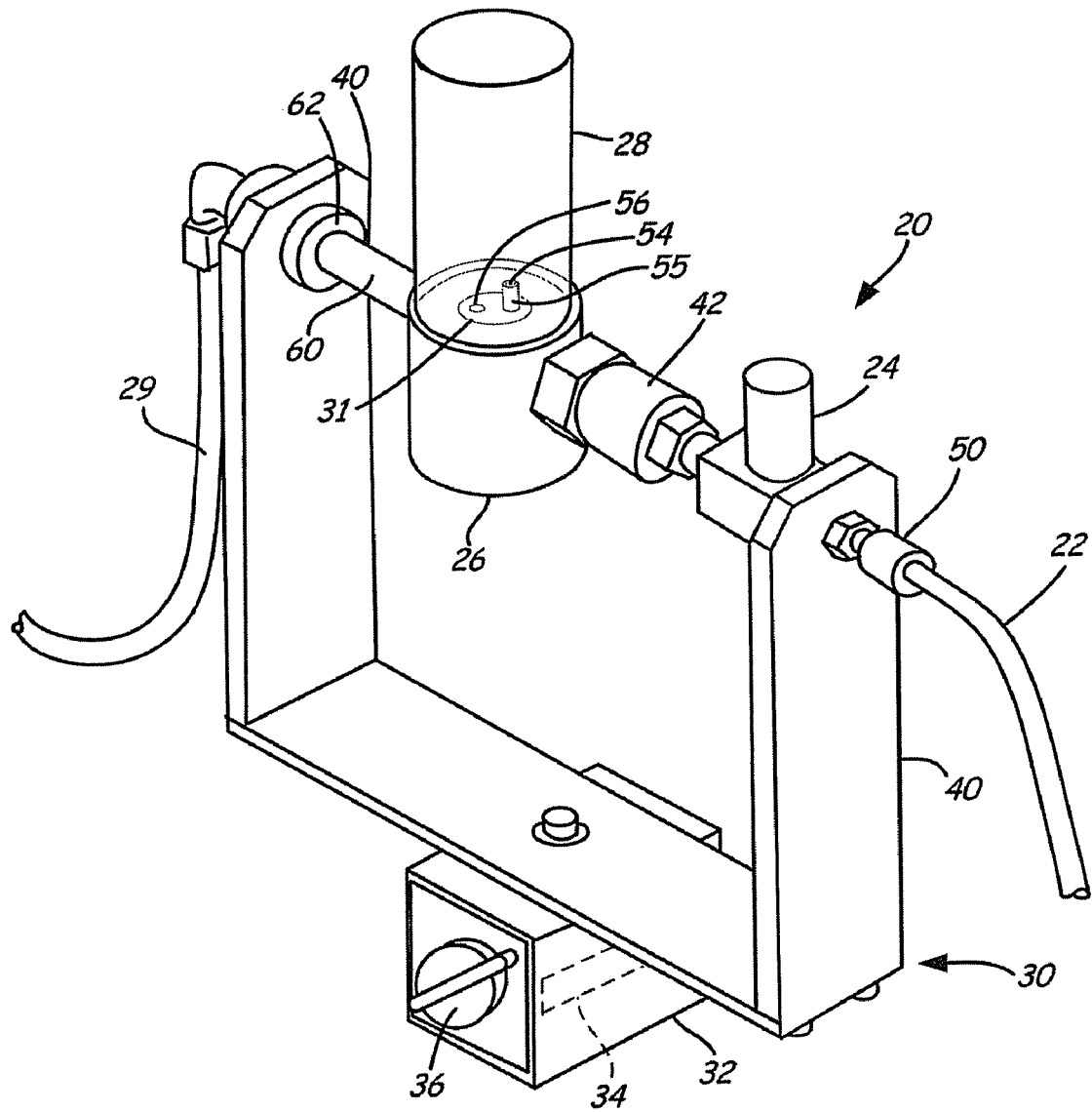
FIG. 3 is a perspective view of the first embodiment of a fluid sampler in the inverted position.

An exemplary hydraulic fluid sampler 20 is illustrated in FIGS. 1-3. The embodiment of FIGS. 1-3 includes additional components explained below that can be beneficial; however, generally, the fluid sampler 20 need only include a supply line 22, a valve 24, such as a needle valve, an invertible sample container holder 26 and a drain line 29 all fluidly coupled together. The sample container holder 26 supports a sample container 28 in a manner so as to receive hydraulic fluid;

however, more importantly, the holder 26 is configured so as to be invertible such that the sample container 28 can be held upside down for a period of time and in a manner that allows the hydraulic fluid to spray the inside of the sample container 28 and thereby flush or rinse the sample container 28. The valve 24 is used to control fluid flow during flushing. After flushing, for example for 15 to 20 minutes, a sample is obtained when the sample container holder 26 is returned to a position where the sample container 28 is in a generally upright position (where an opening of the sample container 28 faces generally upwardly). The valve 24 is used to control fluid flow during filling of the sample container 28 and stop fluid flow when a sufficient volume has been obtained. Using the sampler 20 that allows flushing of the sample container 28 prior to obtaining a sample of hydraulic fluid, obviates the need, and thus the expense, of using hypo-allergenic clean sample containers while still eliminating, or at least substantially minimizing, extraneous contamination of the hydraulic sample in the sample container 28.

In the embodiment illustrated in FIGS. 1-3, the fluid sampler 20 includes a frame 30 that supports the sample container holder 26 in a first position where the sample container 28 is in an inverted position for flushing of the sample container 28 and a second position where the sample container 28 is in a non-inverted position for obtaining a sample. Preferably, the frame 30 also supports the sample container holder 26 in positions transitioning to and from the non-inverted and inverted positions. The frame 20 can be configured to be disposed directly on a suitable surface so as to create a stable support in each position. In the embodiment illustrated, a magnetic base 32 is coupled to the frame 30. The magnetic base 32 includes a magnet 34 (schematically shown) that can be selectively engaged with suitable surface (e.g. ferrous metal) to hold the frame 30 in secure stationary manner. The exemplary magnetic base 32 herein illustrated includes a knob 36 for controlling the position of the magnet 34. Other suitable securing/stabilizing mechanisms for the frame 30 can include a heavy weight and/or a suction cup.

In the embodiment illustrated, the frame 30 is U-shaped having two upstanding supports 40. However, it should be understood that this is but one suitable configuration for the frame 30 in that a single upstanding support could also be used. The support(s) 40 support the sample container holder 26, sample container 28 and hydraulic sample when present in and in between the non-inverted and inverted positions of the sample container holder 26 and sample container 28. One or more rotating hydraulic unions or swivels 42 allowing fluid flow therethrough allow the sample container holder 26 to assume different positions relative to the frame 30.

In the exemplary embodiment, the supply line 22 is connectable through suitable fittings to, if preferred, a high fluid pressure portion of the system under test so as to obtain a sample that is representative of fluid flowing or present in the operating equipment (e.g. servovalves, pumps, actuators) of the system. A fitting 50 at an end remote from the system can be provided to connect the supply line 22 to the valve 24. The fittings on the supply line 22 can be high-pressure quick disconnect fittings, which allows the sampler 20 to be connected/disconnected while the system under test is operating. This is beneficial so as not to impede the operation of the system under test as well as provide a more accurate sampling reflective of the true fluid condition at the time of sampling.

As indicated above, the valve 24 can be a needle valve with flow controlled orificing so as to reduce the pressure in the supply line 22, which may be very high, for example up to 3000 psi. In the embodiment illustrated, the valve 24 is fixedly secured to the frame 30 on one of the supports 40. The valve 24 is fluidly coupled to the swivel 42 that in turn is fluidly coupled to the sample container holder 26. Stated another way, the swivel 42 is disposed and fluidly coupled between the sample container holder 26 and the supply line 22.

In the embodiment illustrated, the sample container holder 26 comprises a base portion 31 having threads configured to threadably mate with threads of the sample container 28. As appreciated by those skilled in the art, other forms of fasteners such as clamps etc. can be used in addition or in the alternative depending on the configuration of the sample container 28. When mounted to the sample container 28 is mounted to the sample container holder 26 two orifices 54 and 56 in the sample container holder 26 open to the inside of the sample container 28. Orifice 54 is fluidly coupled to the valve 24. Orifice 54 is configured so as to provide a fluid stream or spray of hydraulic fluid that will suitably flush the sample container 28 when inverted as explained above. If desired, the orifice 54 can be embodied in a fluted tube 55 that extends further into the sample container 28 and directs the hydraulic fluid up against the inside bottom surface and/or walls of the sample container 28 when inverted. Generally, during flushing, the hydraulic fluid will wash the walls of the sample container 28 as it return by gravity to the sample container holder 26 and exits out of orifice 56 that is fluidly connected to drain line 29, which is typically at atmospheric pressure. In one embodiment, orifice 56 is of size so that hydraulic fluid used to flush the sample container 28 does not build up in the sample container 28. It should be noted that during flushing the sample container holder 26 and sample container 28 can be tilted from side to side if desired to promote flushing on selected surfaces of the sample container 28. In the embodiment illustrated, hydraulic flushing fluid exits the sample container holder 26 into piping 60 that is supported by frame 30 with a rotating hydraulic union or swivel 62, which is fluidly coupled to drain line 29. Stated another way, the swivel 62 is disposed and fluidly coupled between the sample container holder 26 and the drain line 29.

Figure 4:
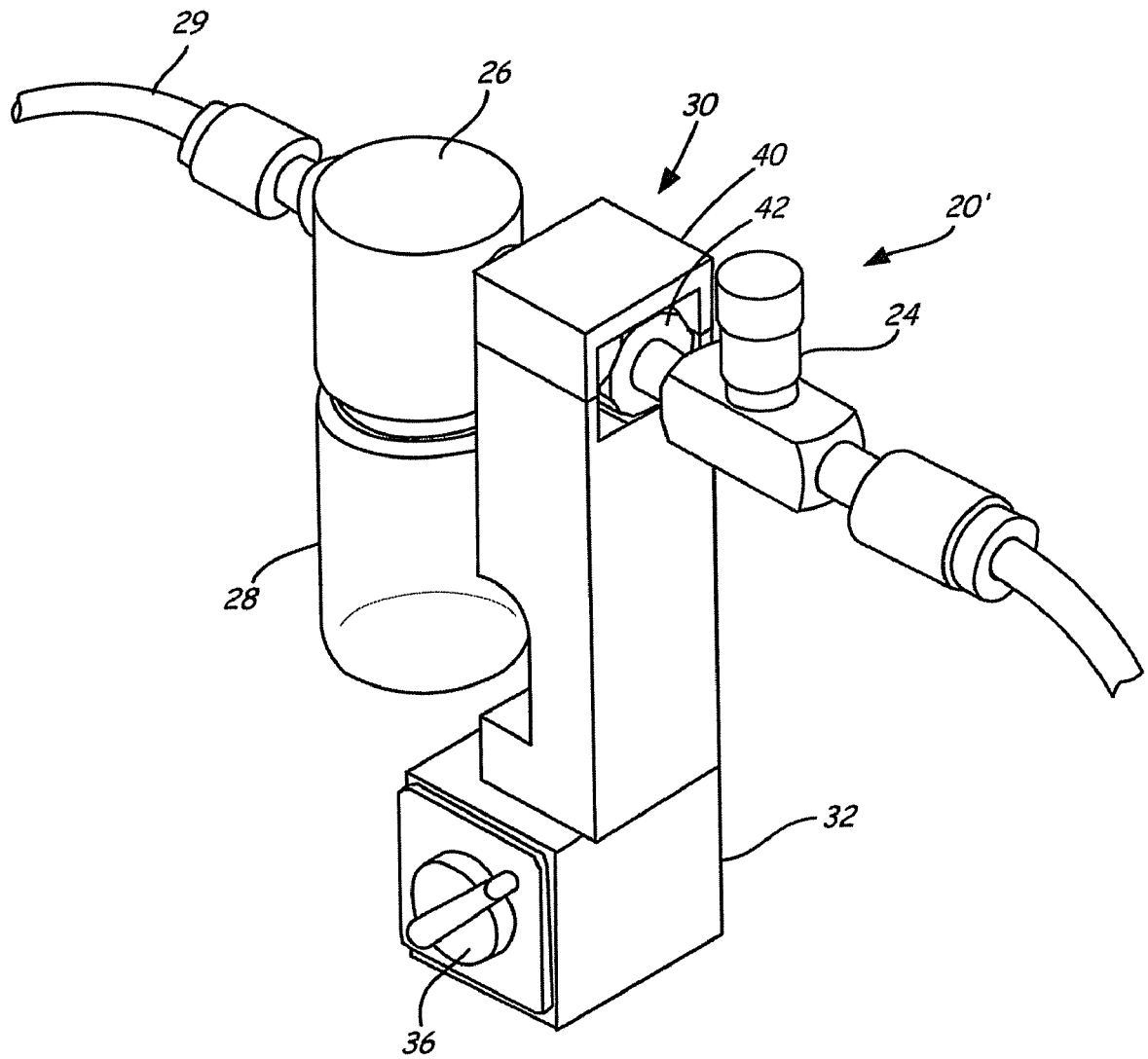
FIG. 4 is a perspective view of a second embodiment of a fluid sampler in a non-inverted position.

FIG. 4 illustrates a second embodiment of a sampler 20' wherein components similar or the same as those described above have been identified with the same reference numbers. In this embodiment, the frame 30 comprises a single support 40. Support 40 supports valve 24 and the rotating hydraulic union 42. One end of the swivel 42 is joined to the sample container holder 26, which can be rotated between a non-inverted position and inverted position in a manner similar to the first embodiment. In this embodiment, the swivel 42 is disposed between the sample container holder 26 and the supply line 22; however, in yet an alternative embodiment, the swivel 42 can be disposed between the sample container holder 26 and the drain line 29.

Figure 5:
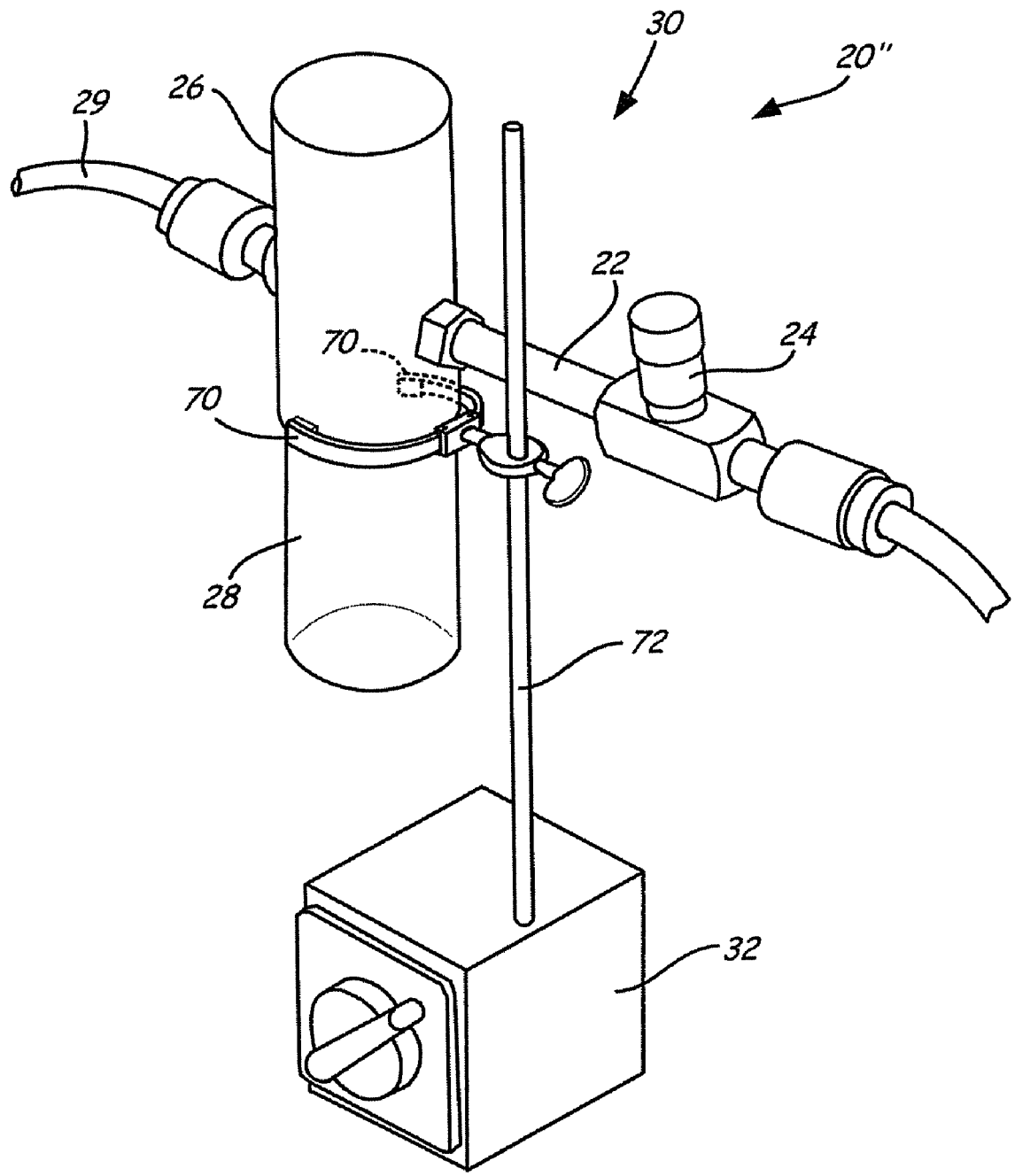
FIG. 5 is a perspective view of third embodiment of a fluid sampler in a non-inverted position.
Figure 6:
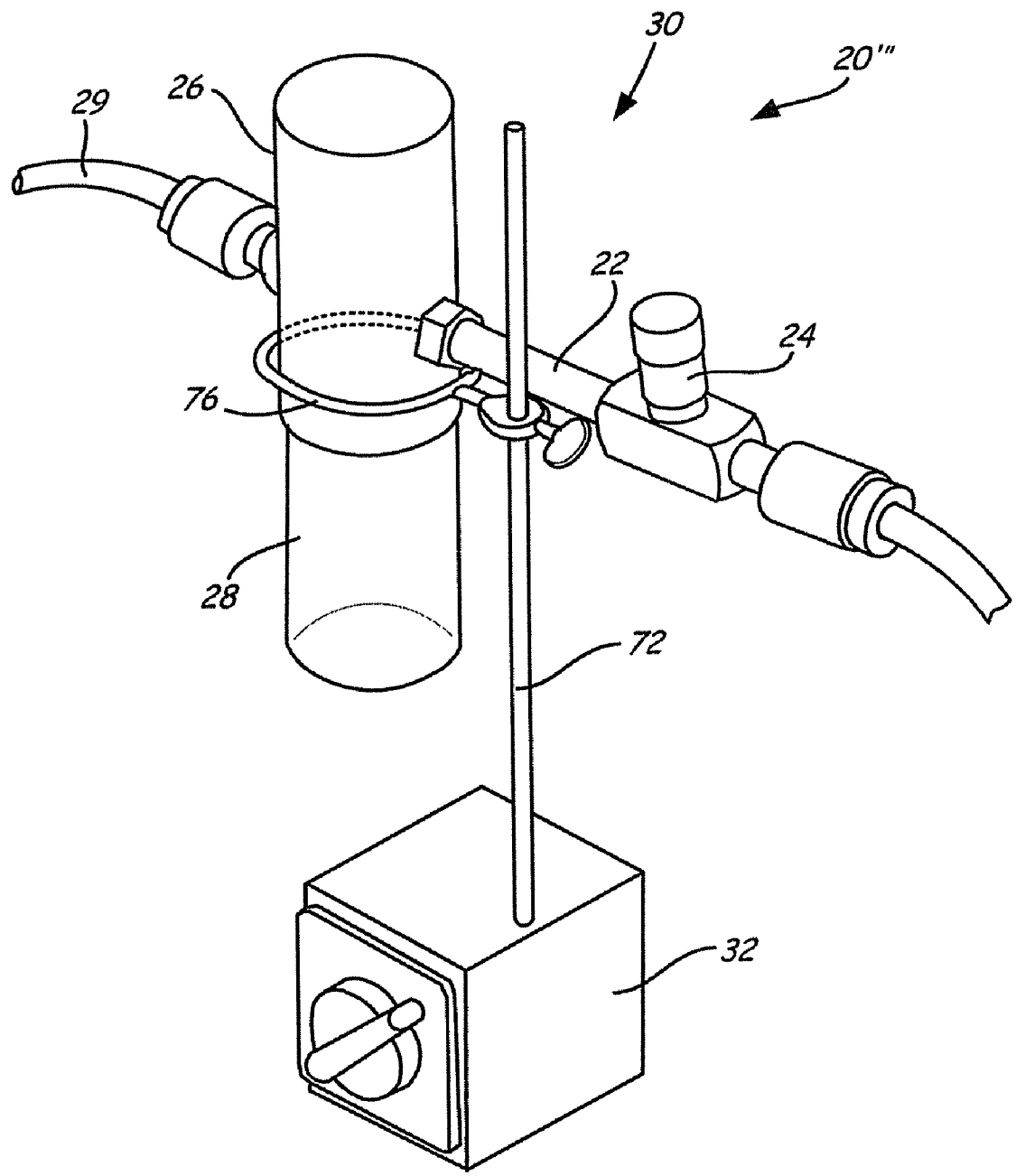
FIG. 6 is a perspective view of fourth embodiment of a fluid sampler in a non-inverted position.
Figure 7:
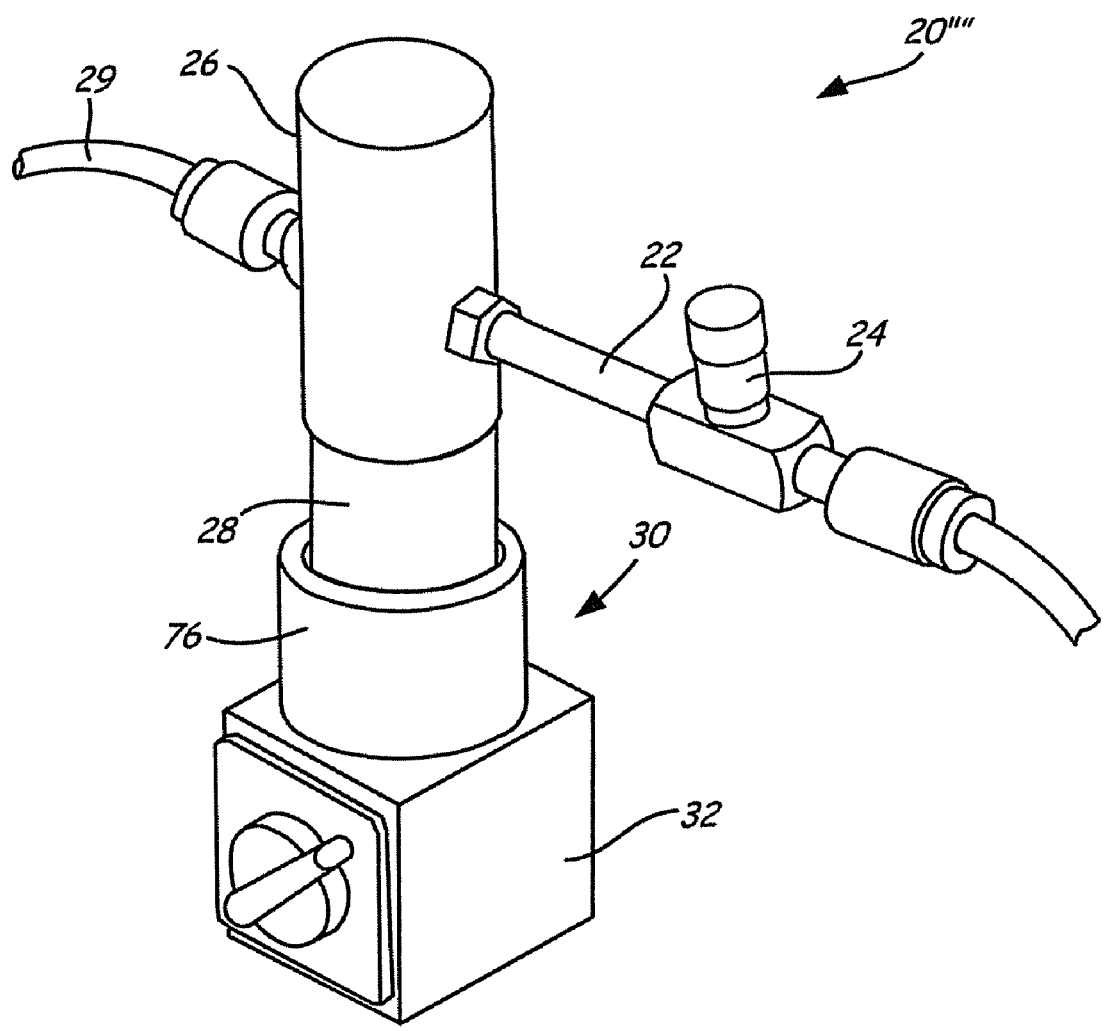
FIG. 7 is a perspective view of fifth embodiment of a fluid sampler in a non-inverted position.

FIGS. 5, 6 and 7 illustrate further embodiments of sampler 20", 20''' and 20'''' wherein components similar or the same as those described above have been identified with the same reference numbers. In each of these embodiments, the frame 30 releasably holds the sample container holder 26 and sample container 28 in each of the inverted (illustrated) and non-inverted (not illustrated) positions. These embodiments obviate the need for a swivel secured to the frame, but rather allow the sample container holder 26 and sample container 28 to be positioned by the user on the frame 30 in each of the inverted and non-inverted positions, wherein portions of the frame 30 releasably engage the sample container holder 26 and/or sample container 28. In FIG. 5, frame 30 includes clamp fingers 70 that form an aperture (partial) into which the sample container holder 26 and/or sample container 28 can be inserted. In this embodiment, the clamp fingers 40 are mounted to an upstanding support 72. In FIG. 6, a hoop 76 is provided on support 72 and comprises an aperture into which each end of the sample container holder 26 and sample container 28 can be inserted. In FIG. 7, frame 30 comprises a cup 78 having an aperture into which each end of the sample container holder 26 and sample container 28 can be inserted. In each of the embodiments of FIGS. 5-7 magnetic base 32 is illustrated; however, this should not be considered limiting in that other devices including suction cups, heavy weight or the like can be used to secure the frame to a support surface. It should also be noted in the embodiments of FIGS. 5-7, valve 24 is disposed in supply line 22 which can have sufficient flexibility to allow operation of the valve 24 in each of the inverted and non-inverted positions. If desired, disconnect couplings can be provided to allow some rotation of the valve 24 relative to the supply line 22. Likewise, if desired, the valve 24 can be mounted to the sample container holder 26 with or without the ability to rotate it thereon.

Figure 8:
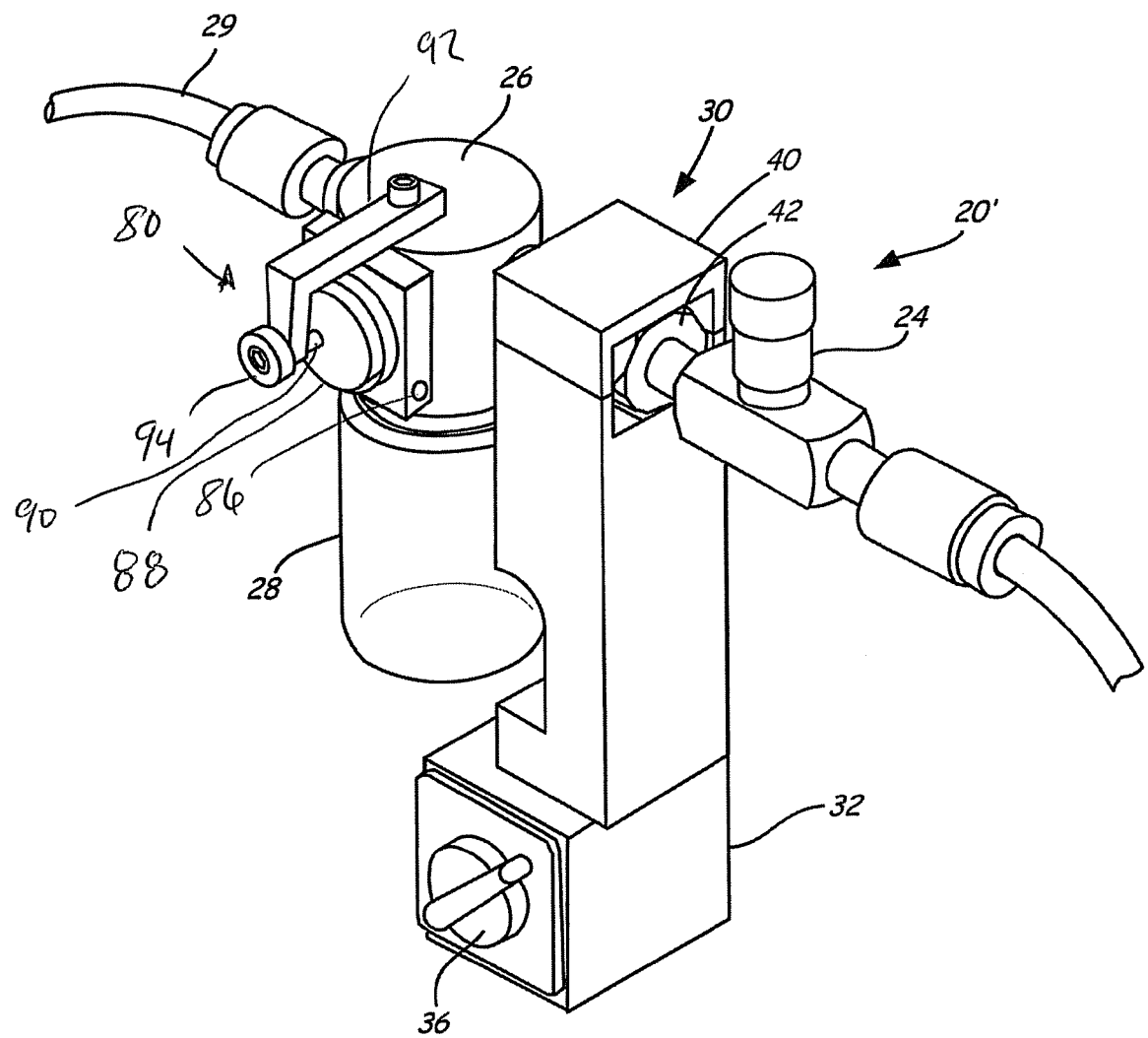
FIG. 8 is a perspective view of a fluid sampler with a sample container cap holder.
Figure 9:
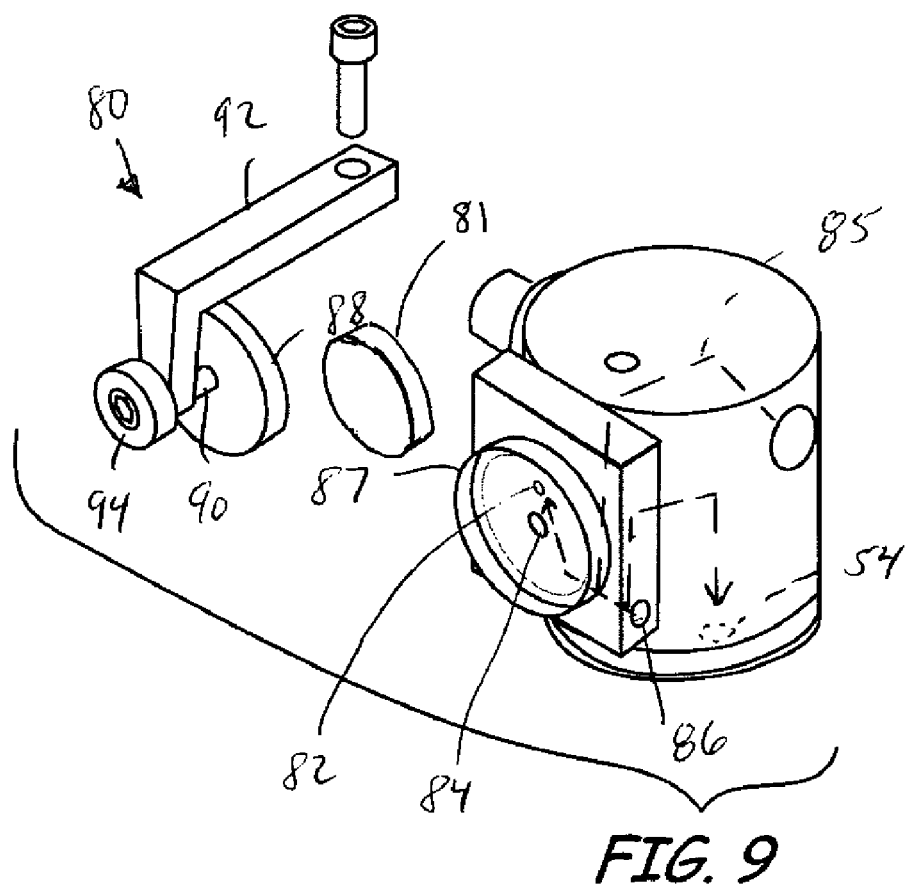
FIG. 9 is a perspective view of a portion of the fluid sampler of FIG. 8 with components removed.

A sample container cap holder 80 is illustrated in FIG. 8. The sample container cap holder 80 is illustrated with sampler 20'; however is should be understood that this is by example only wherein the sample container cap holder can be provided on any of the exemplary samplers herein described as well as others of similar function. The sample container cap holder 80 enables flushing of a cap for the sample container 28. Like the sample container holder 26, the sample container cap holder 80 includes two orifices 82 and 84 (FIG. 9). Orifice 82 selectively receives fluid from supply 22 and is configured so as to spray the inner surfaces of the cap and flush the cap in a manner similar to flushing the container 28. Orifice 84 receives the flushing fluid after flushing the cap and is fluidly coupled to one of the orifices 54 or 56 such that the flushing fluid can collect in the sample container 28. In the alternative, orifice 84 can be fluidly coupled to drain line 29. A valve 86 controls fluid flow to orifice 84. Numerous types of valves can be used. In the embodiment illustrated, the valve 86 comprises a spool valve that moves from left to right and vice versa is used. Suitable passageways 85 (schematically illustrated) are provided in container holder 26 and container cap holder 80 to fluidly couple the spool valve 86 to receive fluid from valve 24 and selectively direct the fluid either to orifice 54 or orifice 82. In the alternative, valve 86 can control fluid only for cap flushing as opposed to redirecting fluid to either the cap or the container 28.

In operation a sample container cap (net shown) 81 is secured to sample container cap holder 80 over orifices 82 and 84. In the embodiment illustrated, the cap 81 is placed in a cap receiver 87 (having orifices 82 and 84) and held in place with plate 88. Plate 88 is coupled to threaded rod 90 that is threaded in a support arm 92 and has a knob 94 remote from plate 88. In this manner, the threads of the sample cap 81 are exposed and can be flushed with fluid. In an alternative embodiment cap receiver 87 can include threads to which threads of the sample cap 81 can threadably mate so as to secure the cap 81 to the receiver 87. Other mechanisms using levers, restraining bars, clamps, clips and the like to hold the sample cap 81 against the receiver 80 and proximate the orifices 82 and 84 can be used. After the cap 81 is secured, the sample container holder 26 can be rotated so as to position orifice 84 in a manner such that when the valve 86 is operated fluid flushes the surfaces of the cap 81 and drains out orifice 84.

Although the subject matter has been described in language specific to structural features and/or methodological acts, it is to be understood that the subject matter defined in the appended claims is not necessarily limited to the specific features or acts described above as has been determined by the courts. Rather, the specific features and acts described above are disclosed as example forms of implementing the claims.

What is claimed is:

1. A hydraulic fluid sampler comprising:
    a supply line;
    a valve fluidly coupled to the supply line;
    a sample container for receiving hydraulic fluid and having a removable cap for a portion thereof;
    a drain line; and
    a sample container holder having a portion configured to cover the portion of the sample container when the cap is removed and when the sample container is mounted to the sample container holder, the sample container holder configured to support the sample container in an inverted position and a non-inverted position, the sample container including a first orifice and a second orifice both disposed in the portion of the sample container holder, the first orifice being configured to flush the sample container with hydraulic fluid when the sample container is in the inverted position, the second orifice configured to receive the flushing hydraulic when the sample container is in the inverted position, the second orifice being fluidly connected to the drain line.

2. The hydraulic fluid sampler of claim 1 and further comprising a frame configured to support the sample container holder in the inverted position and the non-inverted position.

3. The hydraulic fluid sampler of claim 2 and further comprising a swivel allowing fluid flow therethrough, the swivel coupling the sample container holder to the frame and allowing rotation of the sample container holder to obtain the inverted position and the non-inverted position of the sample container.

4. The hydraulic fluid sampler of claim 3 wherein the frame includes a upstanding vertical support, wherein the swivel and the valve are supported by the support.

5. The hydraulic fluid sampler of claim 4 wherein the frame includes two upstanding vertical supports, the sample container holder is disposed between the vertical supports.

6. The hydraulic fluid sampler of claim 5 and further comprising a second swivel allowing fluid flow therethrough, wherein the first-mentioned swivel is fluidly coupled between the sample container holder and the supply line and the second swivel is fluidly coupled between the sample container holder and the drain line.

7. The hydraulic fluid sampler of claim 1 wherein the sample container threadably mates with the sample container holder.

8. The hydraulic fluid sampler of claim 2 and a device adapted to secure the frame to a surface.

9. The hydraulic fluid sampler of claim 2 wherein the device is a magnetic base.

10. The hydraulic fluid sampler of claim 1 and further comprising sample container cap holder having a third orifice fluidly coupled to the supply line to receive fluid, the sample container cap holder configured to hold a sample container cap in a position over third orifice.

11. A hydraulic fluid sampler comprising:
    a supply line;
    a valve fluidly coupled to the supply line;
    a sample container for receiving hydraulic fluid and having a removable cap for a portion thereof;
    a drain line;
    a sample container holder configured to support the sample container in an inverted position and a non-inverted position, wherein the sample container is releasably attached to the sample container holder and wherein the sample container is configured to hold a quantity of hydraulic fluid with the removable cap thereon when the sample container is not attached to the sample container holder; and a frame configured to support the sample container holder in a first position where the sample container is in an inverted position, and configured to support the sample container holder in a second position where the sample container is in a non-inverted position.

12. The hydraulic fluid sampler of claim 11 and further comprising a swivel allowing fluid flow therethrough, the swivel coupling the sample container holder to the frame and allowing rotation of the sample container holder to obtain the inverted position and the non-inverted position of the sample container.

13. The hydraulic fluid sampler of claim 12 wherein the frame includes two upstanding vertical supports, the sample container holder is disposed between the vertical supports.

14. The hydraulic fluid sampler of claim 13 and further comprising a second swivel allowing fluid flow therethrough, wherein the first-mentioned swivel is fluidly coupled between the sample container holder and the supply line and the second swivel is fluidly coupled between the sample container holder and the drain line.

15. The hydraulic fluid sampler of claim 14 wherein the sample container threadably mates with the sample container holder.

16. The hydraulic fluid sampler of claim 15 and a device adapted to secure the frame to a surface.

17. The hydraulic fluid sampler of claim 16 wherein the device is a magnetic base.

18. The hydraulic fluid sampler of claim 11 and further comprising sample container cap holder having an orifice fluidly coupled to the supply line to receive fluid, the sample container cap holder configured to hold a sample container cap in a position over the orifice.

19. A method for obtaining a hydraulic fluid sample from a system, the method comprising:

providing a sample container with a removable cap;
mounting the sample container to a sample container holder;
connecting the sample container holder to the system in order to obtain hydraulic fluid therefrom;
positioning the sample container holder such that the sample container is in an inverted position;
flushing the sample container with hydraulic fluid while the sample container is in an inverted position;
after flushing, positioning the sample container holder such that the sample container is in a non-inverted position;
filling the sample container with a sample of hydraulic fluid;
removing the sample container from the sample container holder, the sample container being configured to hold the sample of hydraulic fluid when the sample container is not attached to the sample container holder; and
securing the removable cap on the sample container to contain the sample of hydraulic fluid.

20. The method of claim 19 wherein the sample container holder is rotatably mounted to a frame and wherein positioning comprises rotating the sample container holder relative to the frame.

21. The method of claim 20 and further comprising releasably securing the frame to a surface.

22. The method of claim 19 and further comprising:
mounting a sample container cap in a position over an orifice that is fluidly coupled to receive hydraulic fluid; and
flushing the sample container cap with hydraulic fluid.

23. The hydraulic fluid sampler of claim 1 wherein the sample container is releasably attached to the sample container holder and wherein the sample container is configured to hold a quantity of hydraulic fluid when the sample container is not attached to the sample container holder.

24. The method of claim 19 and further comprising:
mounting the removable cap to the sample container holder;
flushing the removable cap with hydraulic fluid prior to securing the removable cap on the sample container holder with the sample of hydraulic fluid contained therein.

* * * * *